(12) United States Patent
Michl

(10) Patent No.: US 8,148,570 B2
(45) Date of Patent: Apr. 3, 2012

(54) PROCESS FOR PREPARING VINYL ACETATE WITH UTILIZATION OF THE HEAT OF REACTION

(75) Inventor: Harald Michl, Muehldorf (DE)

(73) Assignee: Wacker Chemie AG, Munich (DE)

( * ) Notice: Subject to any disclaimer, the term of this patent is extended or adjusted under 35 U.S.C. 154(b) by 371 days.

(21) Appl. No.: 12/093,502

(22) PCT Filed: Oct. 30, 2006

(86) PCT No.: PCT/EP2006/067933
§ 371 (c)(1),
(2), (4) Date: May 13, 2008

(87) PCT Pub. No.: WO2007/057297
PCT Pub. Date: May 24, 2007

(65) Prior Publication Data
US 2008/0234511 A1    Sep. 25, 2008

(30) Foreign Application Priority Data
Nov. 15, 2005   (DE) .......................... 10 2005 054 411

(51) Int. Cl.
*C07C 67/48* (2006.01)

(52) U.S. Cl. ........................................ 560/248; 560/231

(58) Field of Classification Search .................. None
See application file for complete search history.

(56) References Cited

U.S. PATENT DOCUMENTS

| 6,258,978 B1 * | 7/2001 | Kitchen et al. ................ 560/248 |
| 6,846,951 B1 | 1/2005 | Thiebaut |
| 6,852,877 B1 | 2/2005 | Zeyss |
| 2005/0238548 A1 | 10/2005 | Van Egmond |

FOREIGN PATENT DOCUMENTS

| DE | 158031 | * | 12/1982 |
| JP | 59162922 | * | 9/1984 |
| JP | 02091044 A | | 3/1990 |
| WO | 2005/092829 A1 | | 10/2005 |

OTHER PUBLICATIONS

Patent Abstract of Japan Corresponding to JP 02091044 A.
Vinylacetate; 00/01-3; Feb. 2002; Nexant Inc./Chem Systems.
Ullmann's Encyclopedia 1996; Chapter "Vinylesters", p. 419-434.
Energy Tips—Steam Systems; US Department of Energy Bulletin; Sep. 2005.
Computers Chem. Engng., vol. 22, No. 7-8, pp. 867-877, 1998; Michael L. Luyben and Björn D. Tyreus.
R. Smith; Chemical Process Design and Integration; Chapter 20, p. 439-444; Chapter 23, p. 465-511; (Sep. 2005).

* cited by examiner

*Primary Examiner* — Sudhakar Katakam
(74) *Attorney, Agent, or Firm* — Brooks Kushman P.C.

(57) ABSTRACT

Vinyl acetate is prepared by
a) continuous gas-phase reaction of ethylene, acetic acid and oxygen at 1 to 30 bar and 130° C. to 200° C., the process heat being removed by heat exchange with water at 120° C. to 185° C. and 1 to 10 bar,
b) the product gas stream consisting essentially of ethylene, vinyl acetate, acetic acid, water, carbon dioxide and further inert gases is fractionated, and
c) all or part of the ethylene is recycled to the recycle gas process, wherein all or part of steam formed in the gas-phase reaction by heat exchange, with a temperature of from 120° C. to 185° C. and pressure of from 1 to 10 bar, is compressed by a differential pressure of at least 0.5 bar and used further.

9 Claims, No Drawings

PROCESS FOR PREPARING VINYL ACETATE WITH UTILIZATION OF THE HEAT OF REACTION

CROSS-REFERENCE TO RELATED APPLICATION

This application is the U.S. national phase of PCT Appln. No. PCT/EP2006/067933 filed Oct. 30, 2006 which claims priority to German application DE 10 2005 054 411.8 filed Nov. 15, 2005.

BACKGROUND OF THE INVENTION

1. Field of the Invention

The invention relates to a process for preparing vinyl acetate in a heterogeneously catalyzed, continuous gas-phase process by reaction of ethylene with acetic acid and oxygen, with utilization of the heat of reaction liberated during the process.

2. Description of the Related Art

Vinyl acetate is prepared in continuous processes with recirculation of the purified product stream. In a heterogeneously catalyzed gas-phase process, ethylene reacts with acetic acid and oxygen over fixed-bed or fluidized-bed catalysts which generally comprise palladium and alkali metal salts on a support material and can additionally be doped with gold, rhodium or cadmium.

The starting materials ethylene, oxygen and acetic acid are reacted in an exothermic reaction, generally at a pressure of from 1 to 30 bar (pressure values here and in the following in bar gauge) and a temperature of from 130° C. to 200° C. in a fixed-bed tube reactor or fluidized-bed reactor to form vinyl acetate:

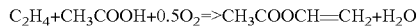

$$C_2H_4 + CH_3COOH + 0.5O_2 => CH_3COOCH=CH_2 + H_2O$$

The ethylene conversion is about 10%, the acetic acid conversion is from about 20 to 30% and the oxygen conversion is up to 90%.

In the preparation of vinyl acetate, a gas mixture consisting predominantly of ethylene, carbon dioxide, ethane, nitrogen and oxygen (recycle gas which generally contains from 60 to 70% by volume of ethylene) is circulated. The gas stream is admixed with the reactants acetic acid, ethylene and oxygen upstream of the fixed-bed tube reactor or fluidized-bed reactor and brought to the reaction temperature by means of heat exchangers operated by means of heating steam. The enrichment of the recycle gas with acetic acid is usually effected by means of an acetic acid saturator or acetic acid vaporizer heated by means of heating steam. After the reaction, the reaction products and unreacted acetic acid are condensed out from the recycle gas and passed to work-up. Product which does not condense out is scrubbed out in a scrubber operated using acetic acid.

The recycle gas or part thereof is freed of carbon dioxide formed before it is once again admixed with the starting materials.

The products vinyl acetate and water and also unreacted acetic acid which have been condensed out are separated from one another in a multistage, usually steam-heated, distillation process. The usual distillation steps are dewatering, azeotropic distillation, pure distillation, by-product removal, wastewater purification, residue work-up and low-boiler and high-boiler removal. The production plants for the work-up of the vinyl acetate can vary.

The reaction temperature in the fixed-bed tube reactor or fluidized-bed reactor of from 130° C. to 200° C. is set by means of evaporative water cooling at a pressure of from 1 to 10 bar. This forms steam, known as process-generated steam, having a temperature of from 120° C. to 185° C. and a pressure of from 1 to 10 bar, preferably from 2.5 to 5 bar. The steam can sometimes be somewhat superheated. In this case, the temperature is higher than the boiling point at the respective process-generated steam pressure. This process-generated steam can then be used for heating further process steps of the vinyl acetate preparation, for example for heating individual distillation columns for the fractionation of the product mixture. Such a procedure is described in JP-A 02-091044.

The reaction temperature is set via the operating pressure of the evaporative water cooling and the process-generated steam formed. The decrease in activity of a catalyst over the operating time is compensated by increasing the reaction temperature, i.e. the operating pressure of the evaporative water cooling and of the process-generated steam formed. The reaction temperature and thus the process-generated steam temperature thus vary over time, which leads to utilization problems with the process-generated steam. To spare the catalyst, to optimize the selectivity and to minimize carbon dioxide formation, the vinyl acetate reaction is operated for as long as possible at a low reaction temperature, corresponding to a low process-generated steam pressure.

A disadvantage here is that the process-generated steam can only be used for heating some of the pressure steps because of its low temperature and pressure level. These are, for example, the dewatering column, wastewater purification, the residue work-up which is usually operated under vacuum, a recycle gas heater and various acetic acid vaporizers and heaters. For the further process steps such as azeotropic distillation or pure distillation, external, higher-grade and often superheated heating steam has to be introduced, usually at a temperature of from 160° C. to 250° C. and a pressure of from 5 bar to 15 bar. A further disadvantage is that cooling of the process reactor in which the exothermic gas-phase reaction takes place produces more process-generated steam than can be consumed in the process steps of vinyl acetate preparation and purification because of the pressure and temperature level of the process-generated steam. It is usually possible to consume only from about 75 to 80% by weight of the process-generated steam formed for heating in process steps. The use of the process-generated steam for process steps depends strongly on the apparatus dimensions selected and the pressure level of the heating steam used for operation of the plant.

The remaining amount can either be condensed, which leads to a complete loss of the energy, or alternatively can be passed on to other operations in an integrated works. However, this is complicated in terms of organization and apparatus. In addition, low-pressure steam is mostly used for heating of selected product pipes or buildings, is therefore subject to fluctuations over the year and can therefore often not be completely utilized further.

SUMMARY OF THE INVENTION

It was therefore an object of the invention to provide a process for preparing vinyl acetate with utilization of the heat of reaction liberated, in which the process-generated steam formed in the exothermic gas-phase reaction can all be used further in the vinyl acetate preparation. These and other objects are achieved by compressing all or part of the steam formed during cooling of the gas phase reaction by a pressure differential of at least 0.5 bar.

DETAILED DESCRIPTION OF THE PREFERRED EMBODIMENT

The invention provides a process for preparing vinyl acetate by means of
a) a heterogeneously catalyzed, continuous gas-phase reaction of ethylene, acetic acid and oxygen at a pressure of from 1 to 30 bar and a temperature from 130° C. to 200° C., with the process heat being removed by heat exchange with water at a temperature of from 120° C. to 185° C. and a pressure of from 1 to 10 bar,
b) fractionation of the product gas stream consisting essentially of ethylene, vinyl acetate, acetic acid, water, carbon dioxide and further inert gases, and
c) recirculation of all or part of the ethylene to the recycle gas process,
characterized in that all or part of the steam (process-generated steam) formed in the gas-phase reaction by heat exchange and having a temperature of from 120° C. to 185° C. and a pressure of from 1 to 10 bar is compressed by a differential pressure of at least 0.5 bar and used further.

The continuous preparation of vinyl acetate is carried out in tube reactors charged with a fixed-bed catalyst or in fluidized-bed reactors using catalysts suitable for the fluidized-bed. Catalysts used are generally supported catalysts doped with noble metals or noble metal salts and promoters, for example bentonite spheres doped with palladium chloride and with Au, Cd and K salts. The reactor is supplied with ethylene, oxygen and acetic acid and the reaction is preferably carried out at a pressure of from 8 to 12 bar and a temperature of from 130° C. to 170° C. Pressure and temperature of the process-generated steam produced are usually from 2.5 to 5 bar and from 140° C. to 160° C. under the preferred reaction conditions. The product gas stream leaving the reactor consists essentially of vinyl acetate, ethylene, acetic acid, water, oxygen, carbon dioxide and the inerts nitrogen, argon, methane and ethane.

The reaction products are condensed out together with the acetic acid added in excess from the product gas stream at the system pressure and scrubbed out with acetic acid in subsequent scrubbing stages. Vinyl acetate, acetic acid, water and further condensable components are subsequently separated from one another by distillation.

The steam (process-generated steam) formed in the gas-phase reaction by heat exchange and having a temperature of from 120° C. to 185° C. and a pressure of from 1 to 10 bar or part thereof is subsequently compressed. Compression can be carried out by means of mechanical compressors. These compress so that no condensation of the steam takes place as a result of the increase in pressure, for example by installation of an upstream, heatable heat exchanger which superheats the steam to prevent condensation.

The process-generated steam is preferably compressed by means of customary steam-jet steam compressors (injector nozzles). This has the advantage that high-pressure steam which is in any case used in the preparation of vinyl acetate for preheating the reaction gas upstream of the reactor can be used. The problems of condensation are not present and the outlay in terms of machinery and apparatus is small. The high-pressure steam passing through the steam-jet steam compressor draws process generated steam in and compresses it. The resulting pressure level is lower than the pressure level of the high-pressure driving steam. Compression occurs virtually adiabatically, so that the total heat content is given by the sum of the heat contents of the two steams which are mixed.

Particular preference is given to using regulated steam-jet steam compressors since these can be matched to the amount of process-generated steam and the pressure level of the process-generated steam to be compressed. In addition, greater flexibility in terms of the final pressure to be reached is possible. Steam-jet steam compressors generally operate according to the Venturi principle. Here, the high-pressure driving steam is introduced into the steam-jet steam compressor and in this is conveyed through a driving nozzle regulated in the jet pump. Process-generated steam is fed into the steam-jet steam compressor via a further feed line. The mixed steam leaves the steam-jet steam compressor through a mixed steam line, with its pressure being determined by means of a pressure gauge. The pressure gauge and the regulator for the driving nozzle are connected via a regulating circuit, so that the desired final pressure of the mixed steam can be set via the regulating valve in the feed line for the high-pressure driving steam. As an alternative, the amount of driving steam fed in can also regulate the driving nozzle. The amount of driving steam has to be sufficiently high for the amount of process-generated steam to be compressed to the desired pressure of the mixture.

As an alternative, the high-pressure driving steam is introduced into the steam-jet steam compressor via a regulating valve. Process-generated steam is fed into the steam-jet steam compressor via a further feed line. The mixed steam leaves the steam-jet steam compressor through a mixed steam line, with its pressure being determined by means of a pressure gauge. The pressure gauge and the regulating valve are connected via a regulating circuit, so that the desired final pressure of the mixed steam can be set via the regulating valve in the feed line for the high-pressure driving steam. Here too, the amount of driving steam fed in can regulate the driving nozzle. The amount of driving steam has to be sufficiently high for the amount of process-generated steam to be compressed to the desired pressure of the mixture.

The final pressure of the process-generated steam which is sought during compression is generally a differential pressure of at least 0.5 bar above the pressure of the process-generated steam. The final pressure of the process-generated steam sought during compression is preferably a differential pressure of up to 10 bar above the pressure of the process-generated steam, more preferably up to 5 bar and most preferably up to 3 bar above the admission pressure of the process-generated steam.

The process-generated steam is preferably compressed to a pressure level of up to 15 bar, more preferably to a pressure level of from 5 to 10 bar.

In the compression of the process-generated steam by means of steam-jet steam compressors, the pressure of the high-pressure driving steam is at least 0.5 bar above the pressure of the process-generated steam, preferably up to 10 bar, particularly preferably up to 20 bar, above the pressure of the process-generated steam. The mixing ratio of high-pressure driving steam to process-generated steam depends on the pressure level of the two steam streams and the desired pressure of the mixture. The weight ratio is generally below 8:1, preferably below 5:1 and most preferably below 3:1.

Owing to the cost structure of modern electricity-heat power stations, the cost difference between low-pressure heating steam at about 5 bar and relatively high-pressure heating steam at about 15 bar is small. This results in the advantage that compression of the process-generated steam by means of relatively high-pressure driving steam at, for example, 15 bar, can be operated so as to require very little driving steam and thus minimize the costs for the heating steam to be sourced externally.

The process of the invention makes it possible to utilize part or all of the process-generated steam produced by means of the heat liberated in the vinyl acetate formation reaction. The compressed process-generated steam can be used further in the vinyl acetate process or be used in other processes. The external sourcing of heating steam for the vinyl acetate production process can thus be significantly minimized.

The following examples illustrate the invention:

COMPARATIVE EXAMPLE 1

A tube reactor equipped with a supported Pd/Au catalyst was supplied with a gas mixture comprising ethylene, acetic acid and oxygen at a pressure of 9.5 bar and a temperature of 160° C.

The reactor was operated with evaporative water cooling. 26.4 tonnes/h of process-generated steam having a pressure of 3.6 bar were formed from the circulating water.

The vinyl acetate formed, water and the excess acetic acid were separated off from the recycle gas leaving the rector and separated from one another in the subsequent distillation and by-products, low boilers and high boilers were also distilled off. The by-product carbon dioxide was separated off from the purified recycle gas, fresh acetic acid, ethylene and oxygen were added to it and the recycle gas was recirculated to the reactor.

The 3.6 bar process-generated steam formed in the evaporative water cooling was used for heating the dewatering column, the wastewater purification, a by-product column, the residue work-up, a recycle gas heater, a vaporizer for the removal of carbon dioxide from the recycle gas and further heat exchangers of the plant.

6.5 tonnes/h of unutilized process-generated steam were passed from the plant to other production operations. In addition, another 19.5 tonnes/h of 5 bar heating steam and 4.4 tonnes/h of 15 bar heating steam were required for heating the further parts of the vinyl acetate production plant.

The externally supplied amount of heating steam was consequently 23.9 tonnes/h.

EXAMPLE 2

The procedure of Example 1 was repeated, with the difference that the 6.5 tones/h of process-generated steam having a pressure of 3.6 bar which were not utilized in the plant were compressed to 5 bar and 193° C. by means of a steam-jet steam compressor using 8.6 tonnes/h of superheated 15 bar driving steam at 248° C. The compressed process-generated steam was additionally used for heating the azeotrope column and purification column.

The compressed process-generated steam was all utilized in the plant.

An additional 4.4 tones/h of 15 bar heating steam were supplied for heating the plant. The total requirement of 15 bar heating steam was 13 tonnes/h. There was no longer any need for 5 bar heating steam for heating within the plant.

The amount of externally supplied heating steam required in Comparative Example 1 was reduced by 10.9 tonnes/h to 13 tonnes/h.

The invention claimed is:
1. A process for preparing vinyl acetate by means of
a) a heterogeneously catalyzed, continuous gas-phase reaction of ethylene, acetic acid and oxygen at a pressure of from 1 to 30 bar and a temperature from 130° C. to 200° C., with the process heat being removed by heat exchange with water at a temperature of from 120° C. to 185° C. and a pressure of from 1 to 10 bar, forming steam,
b) fractionation of the product gas stream consisting essentially of ethylene, vinyl acetate, acetic acid, water, carbon dioxide and further inert gases,
c) recirculation of all or part of the ethylene to the recycle gas process, wherein all or part of the steam formed in the gas-phase reaction by heat exchange and having a temperature of from 120° C. to 185° C. and a pressure of from 1 to 10 bar is compressed by a differential pressure of at least 0.5 bar, and to a pressure of up to 15 bar, and the compressed steam is completely used further in the vinyl acetate preparation process.
2. The process of claim 1, wherein the steam formed in the gas-phase reaction by heat exchange is compressed by a differential pressure of up to 10 bar.
3. The process of claim 1, wherein compression is effected by means of mechanical compressors or by means of steam-jet steam compressors.
4. The process of claim 2, wherein compression is effected by means of mechanical compressors or by means of steam-jet steam compressors.
5. The process of claim 3, wherein high-pressure steam which is used in the preparation of vinyl acetate for preheating the reaction gas upstream of the reactor is used in the compression by means of steam jet steam compressors.
6. The process of claim 1, wherein the steam formed in the gas phase by heat exchange is compressed by a differential pressure of up to 5 bar.
7. The process of claim 1, wherein the steam formed in the gas phase by heat exchange is compressed by a differential pressure of up to 3 bar.
8. The process of claim 1, wherein the steam formed in the gas phase reaction by heat exchange is compressed to a pressure of from 5 to 10 bar.
9. The process of claim 1, wherein a part of the steam formed in the gas phase reaction by heat exchange which is not compressed by a differential pressure of at least 0.5 bar is used for heating one or more portions of a vinyl acetate preparation process selected from the group consisting of wastewater purification, a by-product column, residue work-up, a recycle gas heater, a vaporizer for removal of carbon dioxide from recycle gas, and a heat exchanger.

* * * * *